(12) United States Patent
Tomiya et al.

(10) Patent No.: US 10,531,909 B2
(45) Date of Patent: Jan. 14, 2020

(54) TREATMENT INSTRUMENT

(71) Applicant: OLYMPUS CORPORATION, Hachioji-shi, Tokyo (JP)

(72) Inventors: Hiroto Tomiya, Hanno (JP); Shinya Masuda, Hino (JP); Yuki Kawaguchi, Koshu (JP); Tomoyuki Kaga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/872,613

(22) Filed: Jan. 16, 2018

(65) Prior Publication Data

US 2018/0140350 A1    May 24, 2018

Related U.S. Application Data

(63) Continuation of application No. PCT/JP2016/065050, filed on May 20, 2016.

(30) Foreign Application Priority Data

Jul. 16, 2015 (JP) ................. 2015-142363

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1206* (2013.01); *A61B 2018/0063* (2013.01);
(Continued)

(58) Field of Classification Search
CPC .... A61B 2018/00607; A61B 2018/145; A61B 18/1402; A61B 18/148; A61B 18/1477;
(Continued)

(56) References Cited

U.S. PATENT DOCUMENTS

| 6,273,887 B1 | 8/2001 | Yamauchi et al. |
| 2002/0095152 A1* | 7/2002 | Ciarrocca .......... A61B 18/1402 606/48 |

(Continued)

FOREIGN PATENT DOCUMENTS

| EP | 1 530 952 A1 | 5/2005 |
| JP | H11169381 A | 6/1999 |

(Continued)

OTHER PUBLICATIONS

Aug. 2, 2016 Search Report issued in International Patent Application No. PCT/JP2016/065050.
(Continued)

*Primary Examiner* — Jaymi E Della
*Assistant Examiner* — Sean W Collins
(74) *Attorney, Agent, or Firm* — Oliff PLC

(57) ABSTRACT

A treatment instrument includes a first treatment portion including a first member with a first contact surface and a second member with a second contact surface; a movement mechanism to switch between a closed position where the first and second contact surfaces are close to each other and an open position where the first and second contact surfaces are separated each other; and a second treatment portion juxtaposed to the first treatment portion. A distal end of the second treatment portion is located at a distal side in the longitudinal axis than a distal end of the first treatment portion on the closed position.

17 Claims, 6 Drawing Sheets

(52) U.S. Cl.
CPC ............... *A61B 2018/00083* (2013.01); *A61B 2018/00404* (2013.01); *A61B 2018/00589* (2013.01); *A61B 2018/00607* (2013.01); *A61B 2018/126* (2013.01); *A61B 2018/1253* (2013.01)

(58) Field of Classification Search
CPC . A61B 18/1412; A61B 18/14; A61B 18/1206; A61B 2018/126; A61B 2018/00083; A61B 2018/00404; A61B 2018/0063; A61B 2018/1253; A61B 2018/00589
See application file for complete search history.

(56) References Cited

U.S. PATENT DOCUMENTS

| | | | |
|---|---|---|---|
| 2007/0149968 A1* | 6/2007 | Gonon | A61B 17/3203 606/45 |
| 2009/0112206 A1* | 4/2009 | Dumbauld | A61B 18/1445 606/51 |
| 2010/0100095 A1* | 4/2010 | McClurken | A61B 18/1442 606/48 |
| 2014/0005663 A1* | 1/2014 | Heard | A61B 18/1445 606/41 |

FOREIGN PATENT DOCUMENTS

| | | |
|---|---|---|
| JP | 2001-61848 A | 3/2001 |
| JP | 2004-508875 A | 3/2004 |
| JP | 2005-144192 A | 6/2005 |
| WO | 2000/059392 A1 | 10/2000 |
| WO | 2006/005188 A1 | 1/2006 |

OTHER PUBLICATIONS

Jan. 16, 2018 International Preliminary Report on Patentability issued in International Application No. PCT/JP2016/065050.

Feb. 11, 2019 extended European Search Report issued in European Application No. 16824148.7.

Dec. 20, 2018 Office Action issued in Chinese Application No. 201680003477.2.

Jul. 2, 2019 Office Action issued in Chinese Application No. 201680003477.2.

* cited by examiner

TREATMENT INSTRUMENT

CROSS-REFERENCE TO RELATED APPLICATIONS

This application is a Continuation Application of PCT Application No. PCT/JP2016/065050, filed May 20, 2016 and based upon and claiming the benefit of priority from prior Japanese Patent Application No. 2015-142363, filed Jul. 16, 2015, the entire contents of all of which are incorporated herein by reference.

BACKGROUND OF THE INVENTION

1. Field of the Invention

This invention relates a treatment instrument.

2. Description of the Related Art

For example, Jpn. Pat. Appln. KOKAI Publication No. 2001-61848 discloses a treatment instrument which is able to coagulate a living tissue while sandwiching it between a fixed electrode on the distal side and a movable electrode which slides toward the fixed electrode along the longitudinal axis direction. When, for example, there is a living tissue to be treated in a body cavity or the like, the tissue is treated after the insertion of an endoscope and a treatment instrument through different trocars.

BRIEF SUMMARY OF THE INVENTION

According to one aspect of the present invention, a treatment instrument includes: a sheath which defines a longitudinal axis with a distal end and a proximal end; a first treatment portion which includes a first member including a first contact surface coming into contact with a living tissue and a second member including a second contact surface facing the first contact surface and coming into contact with the living tissue at a position closer to a proximal side than the first contact surface along the longitudinal axis and which is configured to coagulate the living tissue by applying energy to the living tissue sandwiched between the first contact surface and the second contact surface; a movement mechanism which is configured to move at least one of the first member and the second member along the longitudinal axis and to switch between a closed position where the first contact surface is close to the second contact surface and an open position where the first contact surface is separate from the second contact surface; and a second treatment portion which is juxtaposed to the first treatment portion, wherein a distal end of the second treatment portion is located at a position closer to a distal side along the longitudinal axis than a distal end of the first treatment portion when the first contact surface and the second contact surface are located at the closed position, and the distal end of the second treatment portion is located at the same position as the position of the distal end of the first treatment portion or located closer to the proximal side than the distal end of the first treatment portion when the first contact surface and the second contact surface are located at the open position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of this invention will be described with reference to the drawings.

The first embodiment will be described with reference to FIGS. 1A and 1B.

Figure 1A:
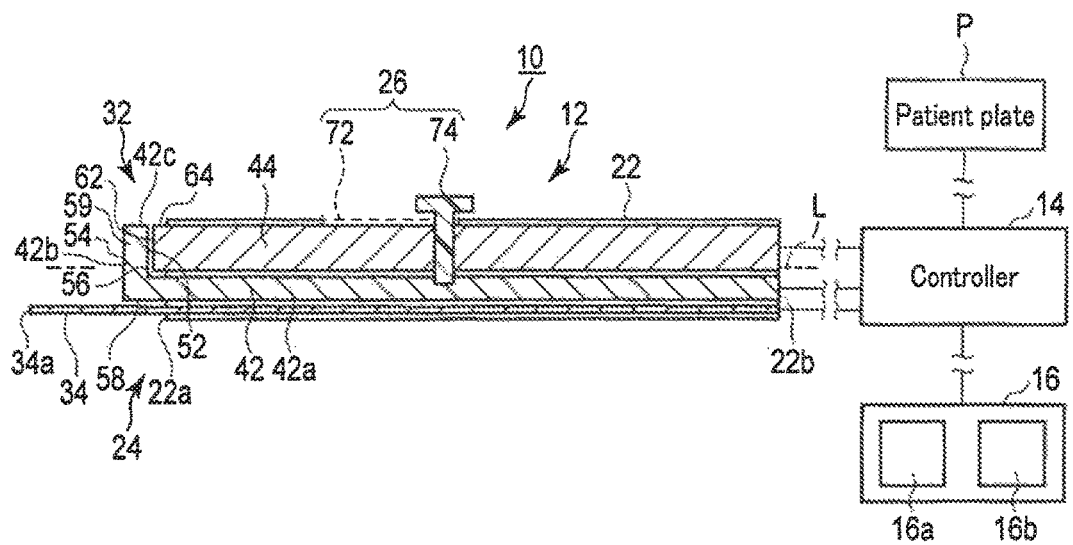
FIG. 1A is a schematic view showing a treatment system according to the first embodiment while a first treatment portion is closed and a distal end of a second treatment portion is made to protrude relative to the first treatment portion toward a distal side along a longitudinal axis.

As shown in FIG. 1A, a treatment system (treatment instrument unit) 10 according to this embodiment includes a treatment instrument 12 and a controller 14. In this case, a foot switch 16 is connected to the controller 14. A hand switch (not shown) can be provided on the treatment instrument 12 together with or instead of the foot switch 16. A patient plate P is also connected to the controller 14.

Figure 1B:
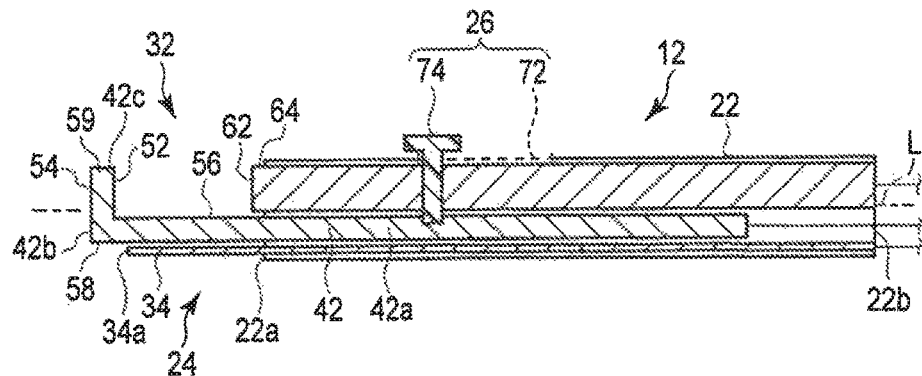
FIG. 1B is a schematic view showing a treatment instrument according to the first embodiment while the first treatment portion is open and the distal end of the second treatment portion is arranged on a proximal side along the longitudinal axis relative to a first contact surface of the first treatment portion.

As shown in FIGS. 1A and 1B, the treatment instrument 12 includes a tubular sheath 22, a treatment region 24 protruding from a distal end 22a of the sheath 22, and a movement mechanism 26. A longitudinal axis L is defined by the distal end 22a and a proximal end 22b of the sheath 22. The sheath 22 has electrical insulation properties. The treatment region 24 includes a first treatment portion 32 and a second treatment portion 34. Referring to FIGS. 1A to 2B, a distal portion of the second treatment portion 34 has a straight shape but is not specifically limited. It is possible to use the second treatment portion 34 having a distal portion formed into an appropriate shape such as a hook-like shape or spatula-like shape.

In this embodiment, the first treatment portion 32 can perform bipolar treatment. The first treatment portion 32 includes a first member 42 and a second member 44. The first member 42 and the second member 44 each are preferably formed from a metal material having electrical conductivity. Note that the first member 42 and the second member 44 may be formed from the same material or different materials. Both the first member 42 and the second member 44 are electrically connected to the controller 14.

In this embodiment, the first member 42 includes a shaft 42a extending, for example, parallel to the longitudinal axis L and an activation portion 42b obtained by bending the distal end of the shaft 42a in a direction crossing the longitudinal axis L. The activation portion 42b is bent in, for example, an almost L shape. Referring to FIGS. 1A to 2B, the angle of the activation portion 42b relative to the shaft 42a is 90°. However, the activation portion 42b may be bent at an appropriate angle other than 90°. Obviously, the portion between portions 54 and 58 (to be described later), i.e., the boundary portion between the shaft 42a and the activation portion 42b, is preferably formed into a curved surface by, for example, being chamfered. Likewise, obviously, the boundary portion between surfaces 52 and 56 is preferably formed into a curved surface by, for example, being chamfered. Like the shaft 42a of the first member 42, the second member 44 extends, for example, parallel to the longitudinal axis L and is formed into, for example, a columnar rod.

The activation portion 42b of the first member 42 includes a first contact surface 52 which treats a living tissue while being in contact with the living tissue. The activation portion 42b of the first member 42 protrudes relative to the distal end 22a of the sheath 22. The first contact surface 52 is directed toward the distal end 22a of the sheath 22. That is, the first contact surface 52 is directed toward the proximal side along the longitudinal axis L.

The second member 44 includes a second contact surface 62 which is located at a proximal side along the longitudinal axis L than the first contact surface 52, which is directed toward the first contact surface 52, and which treats a living tissue, together with the first contact surface 52, while being in contact with the living tissue. The second contact surface 62 is directed toward the distal side along the longitudinal axis L. The first contact surface 52 is preferably parallel to the second contact surface 62.

Obviously, the first contact surface 52 and the second contact surface 62 need not always be directed along the longitudinal axis L, and normal lines to the first contact surface 52 and the second contact surface 62 are preferably formed into slopes shifted from the longitudinal axis L.

In this embodiment, the first contact surface 52 and the second contact surface 62 each are used as a high-frequency electrode. The first contact surface 52 and the second contact surface 62 of the first treatment portion 32 can perform bipolar treatment that can coagulate a living tissue by, for example, sealing the living tissue sandwiched between the first contact surface 52 and the second contact surface 62 by applying energy to the sandwiched living tissue. When the living tissue is a blood vessel, the sandwiched blood vessel is sealed by bipolar treatment.

The first member 42 includes the electrical insulating portion 54 which prevents treatment on a living tissue when energy is applied while being in contact with the living tissue. The electrical insulating portion 54 is formed from, for example, an insulating coating. The electrical insulating portion 54 preferably has heat resistance. The electrical insulating portion 54 is formed on the surface reverse to the first contact surface 52. That is, the electrical insulating portion 54 is located on the distal end surface of the first member 42 and directed toward the distal side along the longitudinal axis L.

The portion 56, of the shaft 42a of the first member 42, which is located near the boundary with the activation portion 42b and also near the distal end of the second member 44 may be formed as an electrode like the first contact surface 52 or may be formed as an electrical insulating portion. The electrical insulating portion 58 is formed on the reverse surface (far face) of the portion 56. The electrical insulating portions 54 and 58 are preferably formed seamlessly and continuously. The electrical insulating portion 58 is formed from, for example, an insulating coating. In addition to the electrical insulating portion 54, the electrical insulating portion 58 of first member 42 prevents treatment on a living tissue when the above energy is applied while being in contact with the living tissue.

The side surfaces between the first contact surface 52 and the electrical insulating portion 54, the side surfaces between the portion 56 and the electrical insulating portion 58, and a far end 42c of the activation portion 42b of the first member 42 relative to the shaft 42a elongated along the longitudinal axis L are preferably formed as electrical insulating portions 59. Note that the far end 42c forms an opening inlet in which a living tissue is arranged between the far end 42c and the second contact surface 62 of the second member 44.

The second member 44 includes an electrical insulating portion 64 which prevents treatment on a living tissue when energy is applied while being in contact with the living tissue. The electrical insulating portion 64 is formed on a portion other than the second contact surface 62. More specifically, an insulating coating is applied to the outer circumferential surface of the portion, of the second member 44, which is located around the longitudinal axis. For this reason, the sliding surface between the first member 42 and the second member 44 is electrically insulated. Note that the electrical insulating portion 64 preferably has heat resistance.

The first member 42 shown in FIGS. 1A and 1B is fixed to the sheath 22. The second member 44 can move along the longitudinal axis L relative to the sheath 22. The movement mechanism 26 can move the second member 44 within a predetermined range along the longitudinal axis L. As the movement mechanism 26, an appropriate mechanism can be used. For example, the movement mechanism 26 as a linear motor can be used to move the second member 44 within a predetermined range along the longitudinal axis L relative to the sheath 22. Briefly described below is an example of the movement mechanism 26 with which the user manually moves the second member 44 along the longitudinal axis L relative to the sheath 22.

The sheath 22 is provided with a slot 72 which is formed longer along the longitudinal axis L than in the circumferential direction of the longitudinal axis L and defines a movement range in which the second member 44 is moved along the longitudinal axis L. The slot 72 is provided with a slide lever (slider) 74 as an operation member. The slide lever 74 can move between the distal end and proximal end of the slot 72 along the longitudinal axis L. The slide lever 74 has electrical insulation properties. The slide lever 74 is coupled to the second member 44. That is, for example, the movement mechanism 26 includes the slot 72 formed in the sheath 22 and the slide lever 74 coupled to the second member 44.

When the user moves the slide lever 74 toward the distal side of the sheath 22 along the longitudinal axis L, the movement mechanism 26 can bring the slide lever 74 into contact with the distal end of the slot 72. When the user moves the slide lever 74 toward the proximal side of the sheath 22 along the longitudinal axis L, the movement mechanism 26 can bring the slide lever 74 into contact with the proximal end of the slot 72. In this manner, the slot 72 can define the movable range of the slide lever 74.

When the user brings the slide lever 74 into contact with the distal end of the slot 72 of the sheath 22 along the longitudinal axis L, the first contact surface 52 of the first member 42 separates from the second contact surface 62 of the second member 44. This sets the open position where the first contact surface 52 of the first member 42 is separate from the second contact surface 62 of the second member 44. When the user brings the slide lever 74 into contact with the proximal end of the slot 72 of the sheath 22 along the longitudinal axis L, the first contact surface 52 of the first member 42 approaches the second contact surface 62 of the second member 44. This sets the closed position where the first contact surface 52 of the first member 42 is close to the second contact surface 62 of the second member 44. At this time, the first contact surface 52 is not in contact with the second contact surface 62, and a slight gap is formed between them. Operating the slide lever 74 can adjust the opening amount by adjusting the distance between the first contact surface 52 and the second contact surface 62. That is, the movement mechanism 26 moves the first member 42 along the longitudinal axis L to switch between the closed position where the first contact surface 52 is close to the second contact surface 62 and the open position where the first contact surface 52 is separate from the second contact surface 62.

The second treatment portion 34 is formed into a rod-like shape thinner than the second member 44. FIGS. 1A to 2B show the second treatment portion 34 extending straight along the longitudinal axis L. As described above, however, the second treatment portion 34 can have any appropriate shape. The second treatment portion 34 is used as, for example, a high-frequency electrode. The second treatment portion 34 can perform bipolar treatment to incise and peel a living tissue between the second treatment portion 34 and the patient plate P attached to the patient by applying energy to the living tissue in contact with the second treatment portion 34.

The second treatment portion 34 is juxtaposed to the first treatment portion 32. When the first treatment portion 32 is switched to the closed position, the second treatment portion 34 is located at the distal side along the longitudinal axis L than the electrical insulating portion 54 of the distal end surface of the first treatment portion 32. When the first contact surface 52 and the second contact surface 62 are located at the closed position, the second treatment portion 34 is located at the distal side along the longitudinal axis L than the first treatment portion 32, and the second treatment portion 34 can incise or peel the living tissue by applying energy to the living tissue.

When the first treatment portion 32 is switched to the open position, the second treatment portion 34 is located at the same position as that of the distal end of the first treatment portion 32 or located at the proximal side than the distal end of the first treatment portion 32. When the first treatment portion 32 is switched to the open position, the second treatment portion 34 is located at the same position as that of the first contact surface 52 of the first treatment portion 32 along the longitudinal axis L or located at the proximal side than the first contact surface 52 of the first treatment portion 32.

Note that the first treatment portion 32 and the second treatment portion 34 are not electrically connected to each other and are electrically insulated. The first treatment portion 32 and the second treatment portion 34 are electrically insulated also by an insulating coating or the like.

In this embodiment, the controller 14 can perform control to perform bipolar treatment using the first treatment portion 32 by outputting energy to the first treatment portion 32 in accordance with, for example, an instruction from the foot switch 16, and can also perform control to cause the second treatment portion 34 to perform monopolar treatment using the second treatment portion 34 by outputting energy to the second treatment portion 34.

The foot switch 16 of the treatment system 10 according to this embodiment includes a first switch 16a and a second switch 16b. The first switch 16a outputs, in accordance with a pressing operation, an instruction to output energy from the controller 14 when the first treatment portion 32 performs bipolar treatment. The second switch 16b outputs an instruction to output energy when the second treatment portion 34 performs monopolar treatment.

The effects of the treatment system 10 according to this embodiment will be briefly described next. For example, the treatment instrument 12 is used together with an endoscope (not shown) via a trocar.

The user attaches the patient plate P to an appropriate location on a patient. The user appropriately holds the treatment instrument 12 and causes the treatment region 24 to face a membrane tissue or layered tissue in the body while checking an observation image of the endoscope. The second treatment portion 34 of the treatment region 24 has a thin shape, and hence can maintain approachability to the membrane tissue or the layered tissue in the body.

As shown in FIG. 1A, the first treatment portion 32 is set at the closed position, and the distal end 34a of the second treatment portion 34 is made to protrude toward the distal side along the longitudinal axis L relative to the distal end of the first treatment portion 32. The user presses the second switch 16b to cause the second treatment portion 34 of the treatment region 24 to perform monopolar treatment on the living tissue. The second treatment portion 34 incises a living tissue as a treatment target or peels tissue layers which is in contact with the second treatment portion 34, by applying monopolar high-frequency energy to the living tissue and recovers a high-frequency current via the patient plate P attached to the patient. Note that the user presses the second switch 16b only when actually performing treatment such as incision, and normally keeps the second switch 16b unpressed.

The first treatment portion 32 and the second treatment portion 34 are electrically insulated. For this reason, in monopolar treatment using the second treatment portion 34, no current flows in the first treatment portion 32. When the electrical insulating portions 54, 58, and 59 of the first treatment portion 32 come into contact with a living tissue at an appropriate position, no current flows in the living tissue in contact with the portions. This prevents a high-frequency current from accidentally flowing from the electrical insulating portions 54, 58, and 59 of the first treatment portion 32 to the living tissue. That is, this prevents the treatment region 24 from performing unintended treatment.

When repeatedly incising a filmy living tissue or peels tissue layers, a blood vessel is sometimes exposed. In this case, the second treatment portion 34 seals the blood vessel, that is, coagulates the blood vessel, to prevent bleeding from the blood vessel.

More specifically, the user operates the slide lever 74 along the slot 72 to switch the first contact surface 52 of the first member 42 and the second contact surface 62 of the second member 44 to the open position, as shown in FIG. 1B. The distal end of the first treatment portion 32 is protruded from the distal end 34a of the second treatment portion 34. More specifically, the first contact surface 52 of the first treatment portion 32 is protruded from the distal end 34a of the second treatment portion 34. This makes it difficult for the distal end 34a of the second treatment portion 34 to obstruct, for example, the operation of bringing the blood vessel into contact with the first contact surface 52 of the first member 42. In this state, the blood vessel is arranged between the first contact surface 52 of the first member 42 of the first treatment portion 32 and the second contact surface 62 of the second treatment portion 34.

As shown in FIG. 1A, the user moves the slide lever 74 to switch the first contact surface 52 of the first member 42 and the second contact surface 62 of the second member 44 to the closed position. At this time, the blood vessel comes into contact with both the first contact surface 52 of the first member 42 and the second contact surface 62 of the second member 44. The first contact surface 52 is not electrically connected to the second contact surface 62. In this state, the user presses the first switch 16a to cause the first treatment portion 32 to perform bipolar treatment on a living tissue as a treatment target such as a blood vessel. The blood vessel (living tissue) as a treatment target which is in contact with both the first contact surface 52 of the first member 42 of the first treatment portion 32 and the second contact surface 62 of the second member 44 is coagulated by Joule heat on applying high-frequency energy to the blood vessel. This prevents bleeding from the coagulated portion. When incising the blood vessel, the user switches the first treatment portion 32 to the open position to release the blood vessel and then switches the portion to the closed position. The coagulated portion of the blood vessel is incised by the second treatment portion 34. At this time, the user is only required to move the treatment region 24 and need not interchange the treatment instrument 12 itself by, for example, removing it from the trocar.

Note that when the user switches the first treatment portion 32 from the open position to the closed position or from the closed position to the open position, the first member 42 and the second member 44 only move back and forth relatively. This leads to a simple structure, which is less likely to degrade visibility when a blood vessel or the like is arranged between the first contact surface 52 of the first member 42 and the second contact surface 62 of the second member 44.

Subsequently, as the user performs monopolar treatment such as incision using the second treatment portion 34, the user performs bipolar treatment using the first treatment portion 32 if, for example, the blood vessel is exposed. If necessary, the user performs monopolar treatment using the second treatment portion 34 to, for example, incise the blood vessel sealed by bipolar treatment, thus finishing the desired treatment.

As described above, the treatment instrument 12 according to this embodiment has the following effects.

When the first contact surface 52 and the second contact surface 62 are located at the closed position, the distal end 34a of the second treatment portion 34 is located closer to the distal side along the longitudinal axis L than the distal end of the first treatment portion 32. This enables the second treatment portion 34 to perform treatment such as incision or peeling, as needed, with respect to a living tissue as a treatment target while the first treatment portion 32 is located at the closed position.

When the first contact surface 52 and the second contact surface 62 are located at the open position, the distal end 34a of the second treatment portion 34 is located at the same position as that of the distal end of the first treatment portion 32 or located closer to the proximal side than the distal end of the first treatment portion 32. Even if, for example, a blood vessel is exposed, when the first treatment portion 32 is switched to the open position, the distal end of the first treatment portion 32, specifically, the first contact surface 52 is able to be arranged closer to the distal side than the distal end 34a of the second treatment portion 34. Thus, it is easy to bring the blood vessel into contact with the first contact surface 52. When the blood vessel is arranged on the first contact surface 52, it is easy to bring the blood vessel into contact with both the first contact surface 52 and the second contact surface 62 while being less likely to be influenced by the presence of the second treatment portion 34. When the first treatment portion 32 is located at the closed position, the distal end 34a of the second treatment portion 34 is located closer to the distal side along the longitudinal axis L than the distal end of the first treatment portion 32; however, when the first treatment portion 32 is switched to the open position, a part of the first treatment portion 32 is located closer to the distal side along the longitudinal axis L than the distal end 34a of the second treatment portion 34. Therefore, using the treatment instrument 12 according to this embodiment makes it easy for the user to perform treatment such as sealing a living tissue such as a blood vessel, as needed, using the first treatment portion 32.

After the blood vessel is sealed, the user can proceed with treatment such as incising or peeling a living tissue as a treatment target using the second treatment portion 34 while maintaining a state in which the treatment region 24 is located close to the living tissue as the treatment target. The user can therefore proceed with treatment on a living tissue as a treatment target using one treatment instrument 12 while maintaining a state in which the treatment region 24 is located close to the living tissue without interchanging the treatment instrument. This can shorten the treatment time and greatly improve the treatment efficiency of a living tissue as a treatment target by using the treatment instrument 12.

When, for example, using the treatment instrument 12 together with an endoscope, there is no need to interchange the treatment instrument 12. This makes it possible to always keep the treatment region 24 close a treatment target while arranging the treatment region 24 within the observation field of view of the endoscope. For this reason, once the user set the treatment region 24 within the field of view of the endoscope, it is not necessary to arrange the treatment region 24 within the field of view of the endoscope again. That is, once the user makes the treatment region 24 face a living tissue as a treatment target, he/she can proceed with treatment while the treatment region 24 is arranged within the field of view of the endoscope.

Note that the treatment system 10 according to this embodiment has been described by exemplifying the case of performing monopolar treatment using the second treatment portion 34. The second treatment portion 34 is formed thinner than the first treatment portion 32. For this reason, the second treatment portion 34 can perform more elaborate treatment than the first treatment portion 32. The second treatment portion 34 can proceed with treatment on a living tissue without requiring the application of any energy from the controller 14, for example, separating an exposed blood vessel from the living tissue by hooking the blood vessel.

The first contact surface 52 of the first member 42 can also be suitably used as a first heater (not shown) instead of a high-frequency electrode. The second contact surface 62 of the second member 44 can also be suitably used as a second heater (not shown) instead of a high-frequency electrode. When the first contact surface 52 and the second contact surface 62 are not used as high-frequency electrodes in this manner, the first contact surface 52 and the second contact surface 62 may come into contact with each other. Note that the first and second heaters each are preferably formed into a plate-like shape which can raise temperature to about several hundred degrees Celsius in several sec. The treatment instrument 12 described here can be used in the same manner as the treatment instrument 12 described in the first embodiment. Using the first and second heaters allows the first treatment portion 32 to perform treatment of coagulating a living tissue or sealing a blood vessel. In addition, using the first and second heaters can incise the living tissue as well as coagulating it, depending on an energy amount setting. In this manner, energy used for treatment using the treatment instrument 12 is not limited to high-frequency energy, and thermal energy can be used as needed.

Note that the treatment instrument 12 may include at least one of the first and second heaters.

The first contact surface 52 of the first treatment portion 32 may be formed as an electrode, while the first heater may be embedded in the first contact surface 52. The second contact surface 62 of the first treatment portion 32 may be formed as an electrode, while the second heater may be embedded in the second contact surface 62. That is, the first contact surface 52 and the second contact surface 62 of the first treatment portion 32 are used both as high-frequency electrodes and heaters. In this case, the first contact surface 52 and the second contact surface 62 are inhibited from coming into contact with each other. A living tissue such as a blood vessel can be coagulated or incised by thermal energy from the heaters while the living tissue is coagulated by high-frequency energy. For example, it takes much time to seal a relatively thick blood vessel or the like using high-frequency energy. However, using both high-frequency energy and thermal energy from the heaters can improve the treatment performance and shorten the time required for sealing the blood vessel.

In addition, heat transfer from the heaters can be used with respect to the second treatment portion 34 instead of performing monopolar high-frequency energy treatment. Using heat transfer can also perform treatment similar to that using high-frequency energy, for example, incision of a living tissue or peeling of tissue layers.

The first modification of the first embodiment will be described next with reference to FIGS. 2A and 2B.

Figure 2A:
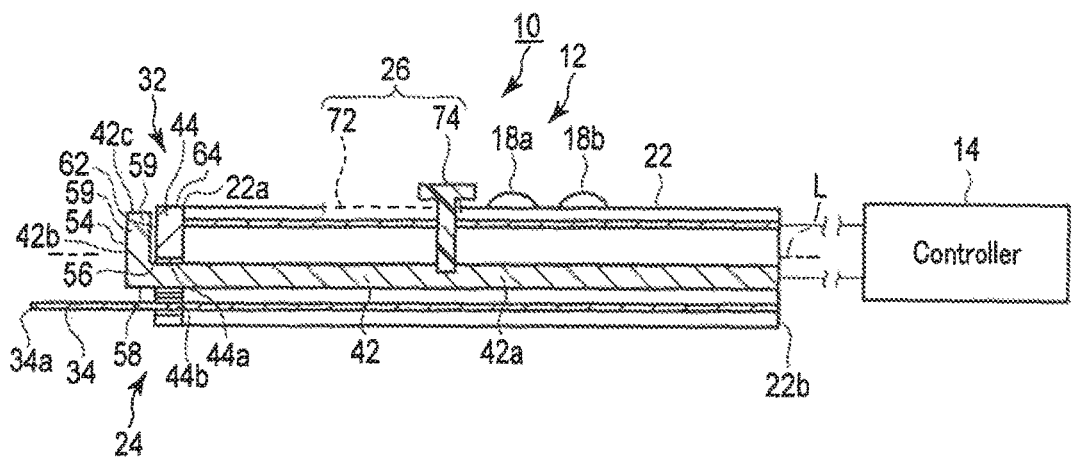
FIG. 2A is a schematic view showing a treatment system according to the first modification of the first embodiment while the first treatment portion is closed and the distal end of the second treatment portion is made to protrude relative to the first treatment portion toward the distal side along the longitudinal axis.
Figure 2B:
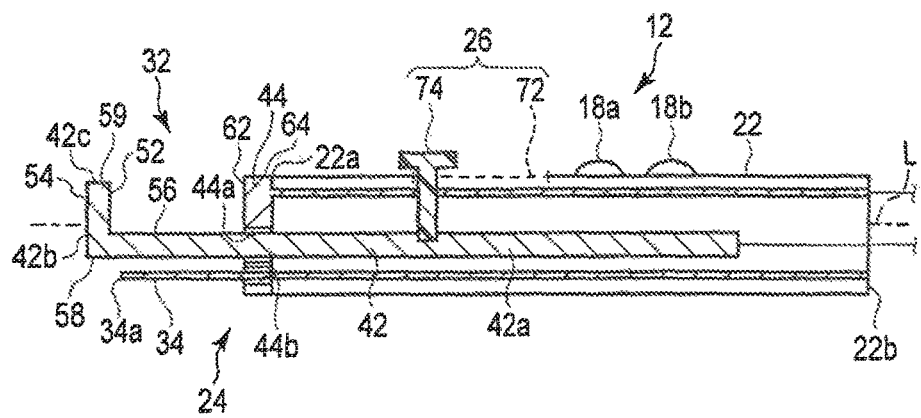
FIG. 2B is a schematic view showing the treatment instrument according to the first modification of the first embodiment while the first treatment portion is open and the distal end of the second treatment portion is arranged at almost the same position along the longitudinal axis as that of the first contact surface of the first treatment portion along the longitudinal axis.

As shown in FIGS. 2A and 2B, the second member 44 is fixed to the distal end of the sheath 22. The second member 44 includes first and second through holes 44a and 44b. The first and second through holes 44a and 44b are preferably provided with insulating coatings. The shaft 42a of the first member 42 extends through the first through hole 44a. The second treatment portion 34 extends through the second through hole 44b. The first member 42 of the first treatment portion 32 is electrically insulated from the second member 44 of the first treatment portion 32. The second treatment portion 34 is electrically insulated from the second member 44 of the first treatment portion 32.

A first switch 18a and a second switch 18b are provided on the outer circumferential surface of the sheath 22. When, for example, the first switch 18a is pressed by the user, the controller 14 outputs an instruction to output energy to perform bipolar treatment using the first treatment portion 32. In addition, when, for example, the second switch 18b is pressed by the user, the controller 14 outputs an instruction to output energy to perform monopolar treatment using the second treatment portion 34. Obviously, in addition to operating the switches 18a and 18b on the outer circumferential surface of the sheath, operating the foot switch 16 can also perform energy output control.

The treatment instrument 12 according to this modification can be used in the same manner as the treatment instrument 12 described in the first embodiment, and hence a description of effects will be omitted.

The second modification of the first embodiment will be described next with reference to FIGS. 3A and 3B.

Figure 3A:
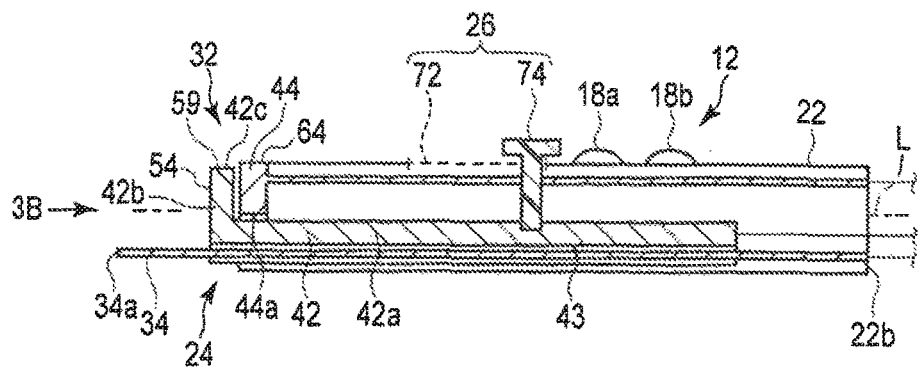
FIG. 3A is a schematic view showing the treatment instrument according to the second modification of the first embodiment while the first treatment portion is closed and the distal end of the second treatment portion is made to protrude relative to the first treatment portion toward the distal side along the longitudinal axis.

As shown in FIG. 3A, the second member 44 is fixed to the distal end of the sheath 22. The second member 44 has a through hole 44a. The through hole 44a is preferably provided with an insulating coating. The shaft 42a of the first member 42 of the first treatment portion 32 extends through the through hole 44a.

Figure 3B:
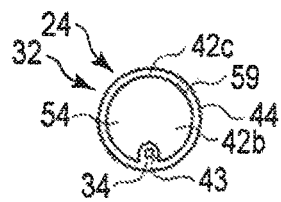
FIG. 3B is a schematic view showing the treatment instrument according to the second modification of the first embodiment when seen from the direction of an arrow 3B in FIG. 3A.

As shown in FIG. 3B, a channel (concave surface) 43 is formed in the shaft 42a of the first member 42 of the first treatment portion 32. The channel 43 is formed into an almost U-shape when seen in a cross-section perpendicular to the longitudinal axis L. The channel 43 extends from the distal end to the proximal end of the shaft 42a. The channel 43 is preferably provided with an insulating coating. The channel 43 is provided with the second treatment portion 34. The first member 42 of the first treatment portion 32 is electrically insulated from the second member 44 of the first treatment portion 32. The second treatment portion 34 is electrically insulated from the first member 42 and the second member 44 of the first treatment portion 32.

The treatment instrument 12 according to this modification can be used in the same manner as the treatment instrument 12 described in the first embodiment, and hence a description of effects will be omitted.

Although the channel 43 has been described as having a U shape, it is obvious that the channel 43 can be formed into a tubular channel. In addition, when, for example, the distal portion of the second treatment portion 34 has a hook shape, the distal end of the channel 43, i.e., the distal end surface of the first member 42 of the first treatment portion 32 preferably has a slot having a shape which can accommodate the distal portion of the second treatment portion 34.

The second embodiment will be described next with reference to FIGS. 4A to 4C. This embodiment is a modification of the first embodiment including each modification. When possible, the same reference numerals as those in the first embodiment denote the same members or members having the same functions as in the second embodiment, and a detailed description of them will be omitted.

Figure 4A:
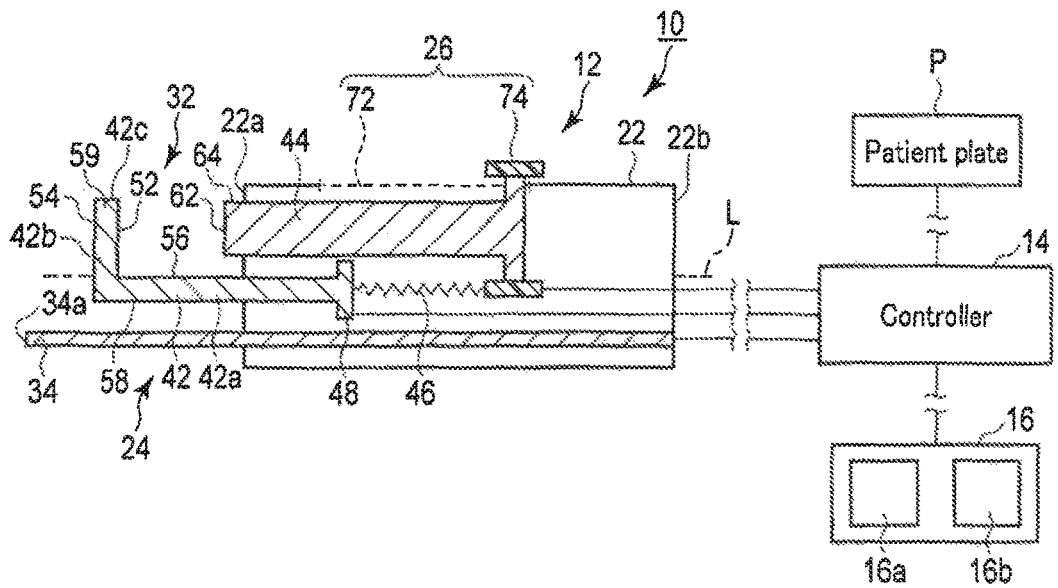
FIG. 4A is a schematic view showing a treatment instrument according to a second embodiment while a first treatment portion is appropriately open and a distal end of a second treatment portion is made to protrude relative to the first treatment portion toward a distal side along the longitudinal axis.
Figure 4B:
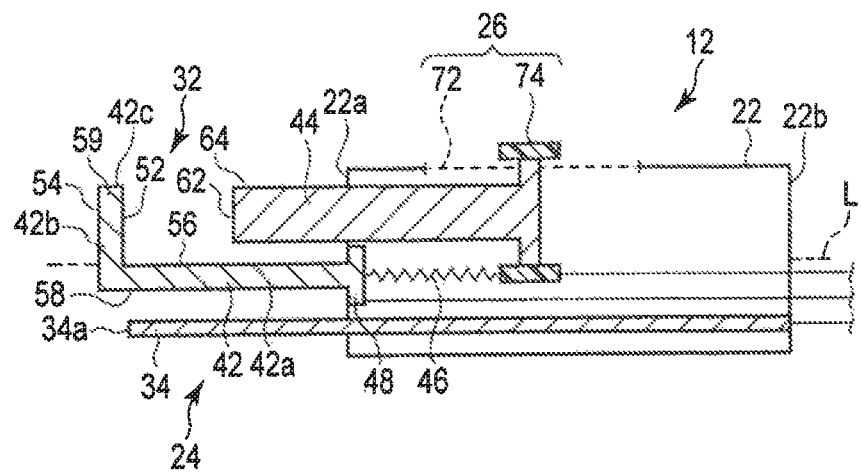
FIG. 4B is a schematic view showing a treatment instrument according to the second embodiment while the first treatment portion is open and the distal end of the second treatment portion is arranged at almost the same position along the longitudinal axis as that of a first contact surface of the first treatment portion along the longitudinal axis.
Figure 4C:
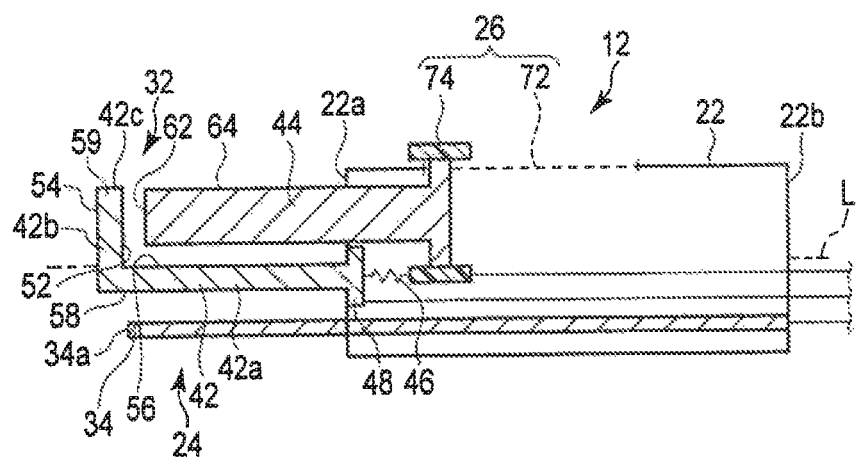
FIG. 4C is a schematic view showing the treatment instrument according to the second embodiment while the first treatment portion is closed and the distal end of the second treatment portion is arranged at almost the same position along the longitudinal axis as that of the first contact surface of the first treatment portion along the longitudinal axis.

As shown in FIGS. 4A to 4C, a slide lever 74 is not fixed to a first member 42 of a first treatment portion 32 but is fixed to a second member 44.

As shown in FIG. 4A, the first member 42 and the second member 44 of the first treatment portion 32 are coupled to each other through an energizing member 46. The portion of the second member 44 which is coupled to the energizing member 46 preferably has electrical insulation properties. For this reason, the first member 42 and the second member 44 are electrically insulated from each other. Note that the energizing member 46 itself is preferably formed from a material having electrical insulation properties. As the energizing member 46, for example, a compression spring such as a compression coil spring is preferably used. For this reason, the energizing member 46 separates a first contact surface 52 of the first member 42 from a second contact surface 62 of the second member 44 of the first treatment portion 32.

The effects of a treatment instrument 12 according to this embodiment will be described next.

As shown in FIG. 4A, the slide lever 74 is arranged at the proximal end of the slot 72. In this case, an engagement portion 48 of the first member 42 is located at the proximal side along a longitudinal axis L than the distal end 22a of the sheath 22. In this case, the distal end 34a of the second treatment portion 34 protrudes toward the distal side along the longitudinal axis L relative to the distal end of the first treatment portion 32. For example, the second treatment portion 34 can perform monopolar treatment such as incising a living tissue or peeling tissue layers.

If, for example, a blood vessel is exposed due to treatment using the second treatment portion 34, the user moves the slide lever 74 from the proximal end to the distal end of the slot 72, as shown in FIG. 4B. The second contact surface 62 of the second member 44 moves toward the distal side along the longitudinal axis L. At this time, the energizing force of the energizing member 46 moves the first member 42 toward the distal side along the longitudinal axis L in conjunction with the second member 44. That is, the energizing member 46 can move the first member 42 and the second member 44 together. The energizing member 46 then keeps the first contact surface 52 of the first member 42 of the first treatment portion 32 separated from the second contact surface 62 of the second member 44.

When the user moves the slide lever 74 from the proximal end to the distal end of the slot 72, the engagement portion 48 of the first member 42 engages with the distal end 22a of the sheath 22. At this time, the first contact surface 52 of the first member 42 is located at almost the same position as that of the distal end 34a of the second treatment portion 34 or located at the distal side than the distal end 34a of the second treatment portion 34. In this state, for example, a blood vessel is brought into contact with the first contact surface 52.

When the user further moves the slide lever 74 from the proximal end to the distal end of the slot 72, the first member 42 engages with the sheath 22 via the engagement portion 48 and is restricted from moving toward the distal side along the longitudinal axis L. The operating force applied to the slide lever 74 by the user moves the second member 44 toward the distal side along the longitudinal axis L against the energizing force of the energizing member 46.

As shown in FIG. 4C, when the user moves the slide lever 74 toward the distal end of the slot 72, the second contact surface 62 of the second member 44 approaches the first contact surface 52 of the first member 42 against the energizing force of the energizing member 46 while the position of the first member 42 relative to the distal end 22a of the sheath 22 is maintained. The slide lever 74 allows the second contact surface 62 of the second member 44 to approach the first contact surface 52 of the first member 42 as the first member 42 moves from the proximal side to the distal side along the longitudinal axis L against the energizing force of the energizing member 46 while engaging with the sheath 22 via the engagement portion 48. That is, the movement mechanism 26 according to this embodiment moves the second member 44 along the longitudinal axis L and can switch between the closed position where the first contact surface 52 is close to the second contact surface 62 and the open position where the first contact surface 52 is separate from the second contact surface 62. This allows the first treatment portion 32 to perform bipolar treatment on a blood vessel. The first treatment portion 32 can therefore seal a blood vessel or the like.

In this manner, when the user operates only the single slide lever 74, both of the first member 42 and the second member 44 can move relative to the sheath 22. The second member 44 can be made to approach the first member 42 by operating the slide lever 74 in accordance with the intention of the user from a state in which the first member 42 engages with the distal end 22a of the sheath 22. For this reason, only moving the slide lever 74 relative to the sheath 22 can move the second member 44 along the longitudinal axis L and perform appropriate treatment using the first treatment portion 32 while the first member 42 is positioned.

This embodiment has exemplified the case in which one end of the energizing member 46 is coupled to the first member 42, and the other end is coupled to the second member 44. Even if, however, one end of the energizing member 46 is coupled to the first member 42 and the other end is coupled to the slide lever (slider) 74, the first member 42 and the second member 44 can be moved in the same manner as described above.

The third embodiment will be described with reference to FIGS. 5A to 5C. This embodiment is a modification of the first and second embodiments. When possible, the same reference numerals as those in the first and embodiments denote the same members or members having the same functions as in the third embodiment, and a detailed description of them will be omitted.

The first embodiment has exemplified the case in which the first contact surface 52 of the first member 42 can be located at the same position as that of the distal end 34a of the second treatment portion 34 or located closer to the distal side than the distal end 34a of the second treatment portion 34 by moving the first member 42 of the first treatment portion 32 relative to the distal end 22a of the sheath 22 along the longitudinal axis L. The second embodiment has exemplified the case in which the first contact surface 52 of the first member 42 can be located at the same position as that of the distal end 34a of the second treatment portion 34 or located closer to the distal side than the distal end 34a of the second treatment portion 34 by moving the first member 42 and the second member 44 of the first treatment portion 32 relative to the distal end 22a of the sheath 22 along the longitudinal axis L.

Figure 5A:
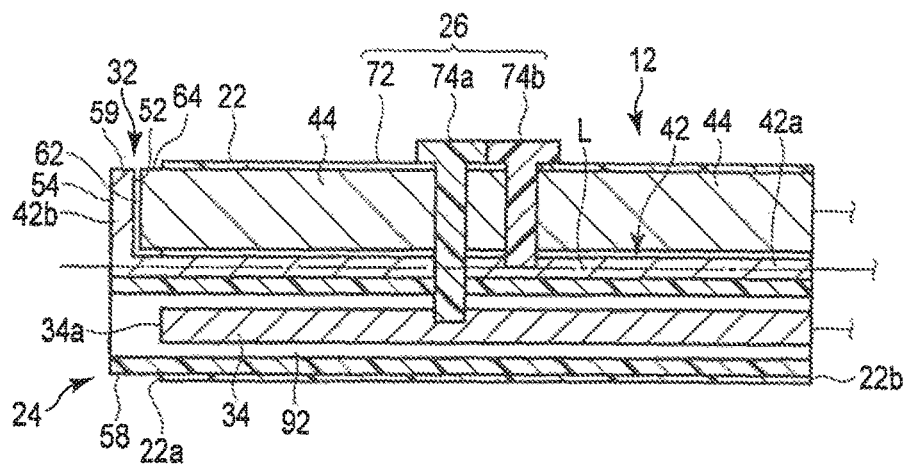
FIG. 5A is a schematic view showing a state in which the movement mechanism of a treatment instrument according to a third embodiment is operated to switch a first treatment portion in a treatment region to a closed position, and a second treatment portion is pulled into the first treatment portion.
Figure 5B:
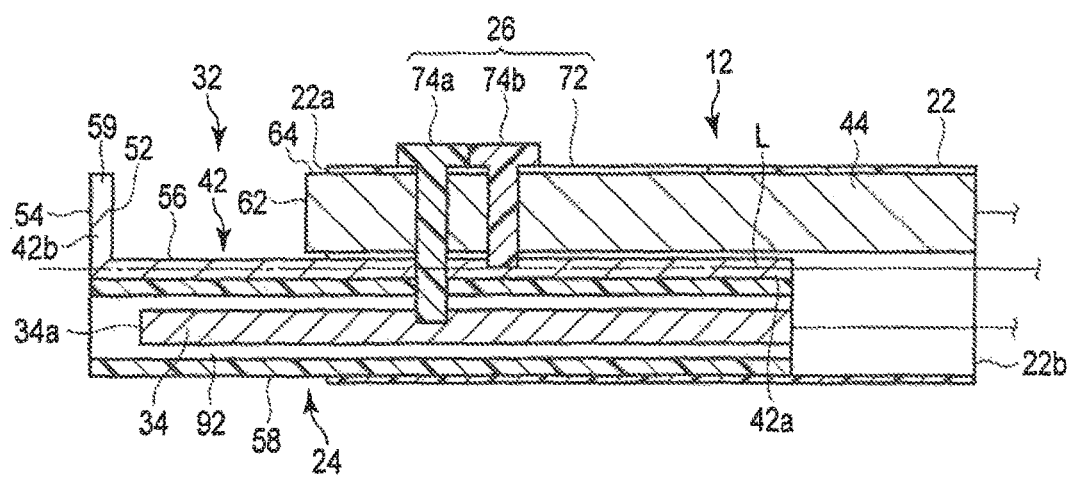
FIG. 5B is a schematic view showing a state in which the movement mechanism of the treatment instrument according to the third embodiment is operated to switch the first treatment portion in the treatment region to an open position, and the second treatment portion is pulled into the first treatment portion.
Figure 5C:
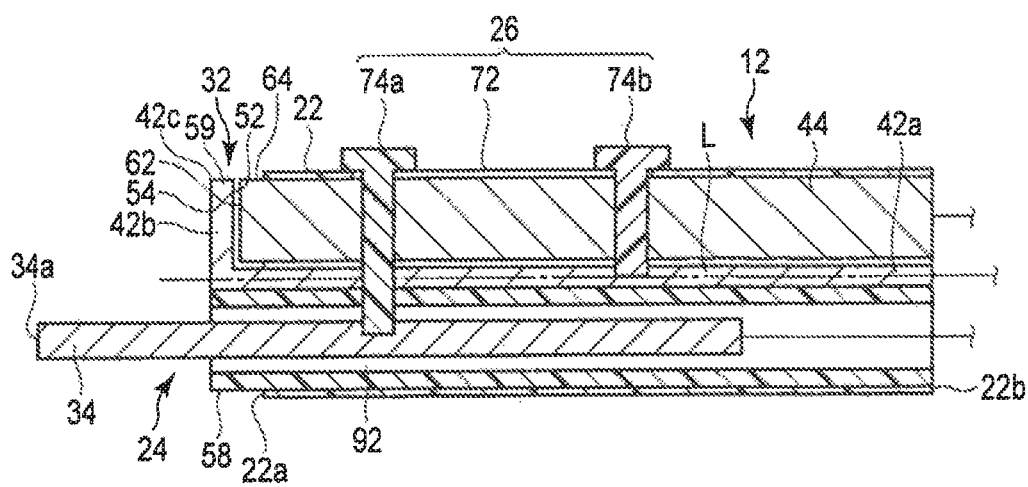
FIG. 5C is a schematic view showing a state in which the movement mechanism of the treatment instrument according to the third embodiment is operated to switch the first treatment portion in the treatment region to the closed position, and the second treatment portion is made to protrude relative to the distal end of the first treatment portion.

As shown in FIGS. 5A to 5C, the second treatment portion 34 may be made movable relative to the distal end 22a of the sheath 22 along the longitudinal axis L. That is, the amount of protrusion of the distal end 34a of the second treatment portion 34 relative to the distal end 22a of the sheath 22 may be made adjustable. This also makes it possible to locate the first contact surface 52 of the first member 42 of the first treatment portion 32 at the same position as that of the distal end 34a of the second treatment portion 34 or at a position closer to the distal side than the distal end 34a of the second treatment portion 34.

The first member 42 of the first treatment portion 32 includes a channel 92 formed parallel to the longitudinal axis L and having an insulated inner circumferential surface. In this case, the channel 92 is formed in the surface reverse to a portion 56.

A movement mechanism 26 includes the slot 72, the first slide lever 74a, and a second slide lever 74b. The slot 72 is commonly used for the first slide lever 74a and the second slide lever 74b. The first slide lever 74a is arranged closer to the distal side in the slot 72 along the longitudinal axis L than the second slide lever 74b. The first slide lever 74a is coupled to the second treatment portion 34. The second slide lever 74b is coupled to the shaft 42a of the first member 42 of the first treatment portion 32.

When no treatment is to be performed, the first slide lever 74a and the second slide lever 74b are located closest to the proximal side in the slot 72, as shown in FIG. 5A. That is, the first treatment portion 32 is switched to the closed position, and the second treatment portion 34 is located closer to the proximal side than the distal end of the activation portion 42b of the first member 42 of the first treatment portion 32.

When the first treatment portion 32 seals a blood vessel or the like, the first slide lever 74a and the second slide lever 74b are located closest to the distal side in the slot 72, as shown in FIG. 5B. That is, the first treatment portion 32 is switched to the open position, and the second treatment portion 34 is located closer to the proximal side than the distal end of the activation portion 42b of the first member 42 of the first treatment portion 32.

When the second treatment portion 34 incises a membrane or peels a living tissue, the first slide lever 74a is located closest to the distal side in the slot 72, and the second slide lever 74b is located closest to the proximal side, as shown in FIG. 5C. That is, the first treatment portion 32 is switched to the closed position, and the second treatment portion 34 is made to protrude relative to the distal end of the activation portion 42b of the first member 42 of the first treatment portion 32. This allows the second treatment portion 34 to protrude to the distal side along the longitudinal axis L relative to the first member 42 of the first treatment portion 32.

While the user performs treatment using the treatment instrument 12 when the treatment region 24 is arranged at an appropriate position, the user moves the first and second slide levers 74a and 74b of the movement mechanism 26 to the state shown in FIG. 5A or the state shown in FIG. 5C.

The user then moves the first and second slide levers 74a and 74b to the state shown in FIG. 5C, and makes the second treatment portion 34 protrude relative to the distal end of the activation portion 42b of the first member 42 of the first treatment portion 32. In this state, for example, the user presses the second switch 16b of the foot switch 16 to perform monopolar treatment on a living tissue using the second treatment portion 34 of the treatment region 24. The second treatment portion 34 incises a living tissue such as a membrane or peels tissue layers which is in contact with the second treatment portion 34.

If, for example, a blood vessel is exposed, the user moves the first and second slide levers 74a and 74b to the state shown in FIG. 5B to switch the first treatment portion 32 to the open position and pull the second treatment portion 34 into the channel 92 relative to the first treatment portion 32. In this state, the blood vessel is arranged between the first contact surface 52 of the first member 42 of the first treatment portion 32 and the second contact surface 62 of the second treatment portion 34. When the user moves the first and second slide levers 74a and 74b to the state shown in FIG. 5A or 5C to switch the first treatment portion 32 to the closed position, the blood vessel is brought into contact with both the first contact surface 52 of the first member 42 and the second contact surface 62 of the second member 44. In this state, for example, the user presses the first switch 16a of the foot switch 16 to perform bipolar treatment on a living tissue as a treatment target such as a blood vessel using the first treatment portion 32, thus sealing the blood vessel.

As described above, when, for example, the first treatment portion 32 performs treatment, the second treatment portion 34 can be accommodated in the first treatment portion 32, as shown in FIGS. 5A and 5B. This can prevent the second treatment portion 34 from becoming an obstruction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
   a sheath which defines a longitudinal axis with a distal end and a proximal end;
   a first treatment portion which includes:
      a first member including a first contact surface that is configured to come into contact with a living tissue, and a second member including a second contact surface that faces the first contact surface, and is configured to come into contact with the living tissue at a position proximal of the first contact surface along the longitudinal axis, the first treatment portion being configured to coagulate the living tissue by applying a first energy to the living tissue sandwiched between the first contact surface and the second contact surface;

a movement mechanism which is configured to move at least one of the first member or the second member along the longitudinal axis to switch between:
  an open position where the first contact surface is separated from the second contact surface, and
  a closed position where the first contact surface is closer to the second contact surface than in the open position, and the first contact surface and the second contact surface are configured to contact the living tissue; and a second treatment portion which is fixed to the sheath and juxtaposed to the first treatment portion such that the second treatment portion is disposed entirely on a radial outer side of the first treatment portion, wherein:
  a distal end of the second treatment portion is located at a position distal of a distal end of the first treatment portion when the first contact surface and the second contact surface are in the closed position,
  the distal end of the second treatment portion is located at a position that is: the same position as the position of the distal end of the first treatment portion, or proximal of the distal end of the first treatment portion when the first contact surface and the second contact surface are in the open position, and
  the second treatment portion is configured to be switched between the position distal of the distal end of the first treatment portion and the position that is the same position as or proximal of the position of the distal end of the first treatment portion without moving relative to the first treatment portion.

2. The treatment instrument of claim 1, wherein the second treatment portion is configured to incise or peel the living tissue by applying a second energy to the living tissue.

3. The treatment instrument of claim 1, wherein the movement mechanism includes:
  a slider which is coupled to the second member and which is movable along the longitudinal axis of the sheath; and
  an energizing member having one end coupled to the first member and the other end coupled to one of the slider and the second member.

4. The treatment instrument of claim 3, wherein the energizing member is configured to move the first member and the second member together.

5. The treatment instrument of claim 4, wherein:
  the first member includes an engagement portion whose position is defined relative to the sheath when the slider moves from a proximal side to a distal side along the longitudinal axis, and
  the slider is configured to make the second contact surface of the second member approach the first contact surface of the first member as the slider moves from the proximal side to the distal side along the longitudinal axis against an energizing force of the energizing member while the first member engages with the sheath via the engagement portion.

6. The treatment instrument of claim 1, wherein the first member of the first treatment portion includes a channel in which the second treatment portion is arranged.

7. The treatment instrument of claim 1, wherein the distal end of the second treatment portion is located at a distal-most position of the instrument when the first contact surface and the second contact surface are in the closed position.

8. The treatment instrument of claim 1, wherein:
  an electrical insulating portion is provided at the distal end of the first treatment portion, and
  the second treatment portion is configured to protrude to a distal side with respect to a distal end of the electrical insulating portion when the first treatment portion is in the closed position.

9. The treatment instrument according to claim 1, wherein the second treatment portion radially overlaps at least one of the first contact surface and the second contact surface regardless of whether the first member and the second member are in the open position or the closed position.

10. The treatment instrument according to claim 1, wherein a sliding surface between the first member and the second member is electrically insulated.

11. The treatment instrument according to claim 1, wherein:
  the first member is fixed with respect to the sheath,
  the second member is movable with respect to the sheath,
  the movement mechanism includes a slot formed in the sheath and a slide lever coupled to the second member,
  the slide lever is configured to be moved between a first end and a second end of the slot to move the second member to switch between the open position and the closed position, and
  a gap is formed between the first contact surface and the second contact surface in the closed position.

12. A treatment instrument comprising:
  a sheath that defines a longitudinal axis with a distal end and a proximal end;
  a first treatment portion that includes a first bipolar electrode and a second bipolar electrode provided at the distal end of the sheath, and is configured to apply high frequency energy to a living tissue sandwiched between the first bipolar electrode and the second bipolar electrode;
  a second treatment portion that includes a monopolar electrode provided at the distal end of the sheath, and is configured to apply high frequency energy to the living tissue by the monopolar electrode, the second treatment portion being juxtaposed to the first treatment portion such that the second treatment portion is disposed entirely on a radial outer side of the first treatment portion; and
  a movement mechanism that is configured to move a relative position of the first treatment portion and the second treatment portion along the longitudinal axis;
  wherein:
  the movement mechanism is configured to switch between:
    a first position where the first bipolar electrode is located on a distal side with respect to the monopolar electrode and the first treatment portion is configured to apply the high frequency energy to the living tissue; and a second position where the first bipolar electrode is located on a proximal side with respect to the monopolar electrode and the second treatment portion is configured to apply the high frequency energy to the living tissue; and the movement mechanism is configured to switch between the first position and the second position without the monopolar electrode moving relative to the first treatment portion.

13. The treatment instrument according to claim 12, wherein the first treatment portion further comprises an electrical insulating surface formed on an opposite side surface of the first bipolar electrode, and the monopolar electrode is located on a distal side with respect to the electrical insulating surface when in the second position.

14. The treatment instrument according to claim 12, wherein the second treatment portion radially overlaps at least one of the first bipolar electrode and the second bipolar electrode regardless of whether the movement mechanism is in the first position or the second position, and the second treatment portion is fixed to the sheath.

15. The treatment instrument according to claim 12, wherein a sliding surface between the first bipolar electrode and the second bipolar electrode is electrically insulated.

16. The treatment instrument according to claim 12, wherein:
  the first bipolar electrode is fixed with respect to the sheath,
  the second bipolar electrode is movable with respect to the sheath,
  the movement mechanism includes a slot formed in the sheath and a slide lever coupled to the second bipolar electrode,
  the slide lever is configured to be moved between a first end and a second end of the slot to move the second bipolar electrode to switch between the first position and the second position, and
  a gap is formed between the first bipolar electrode and the second bipolar electrode in the second position.

17. A treatment system comprising:
  the treatment instrument according to claim 12;
  a controller that is configured to perform:
    a bipolar treatment by outputting energy via the first bipolar electrode and the second bipolar electrode; and
    a monopolar treatment by outputting energy via the monopolar electrode; and
  a foot switch that is configured to instruct the controller to switch between the bipolar treatment and the monopolar treatment.

* * * * *